United States Patent [19]

Nichols

[11] Patent Number: 5,712,107
[45] Date of Patent: Jan. 27, 1998

[54] SUBSTITUTES FOR MODIFIED STARCH AND LATEXES IN PAPER MANUFACTURE

[75] Inventor: Scott Edward Nichols, Johnston, Iowa

[73] Assignee: Pioneer Hi-Bred International, Inc., Des Moines, Iowa

[21] Appl. No.: 485,243

[22] Filed: Jun. 7, 1995

[51] Int. Cl.$^6$ .................. C12Q 1/48; C12Q 1/00; C12Q 1/34; C07H 1/00

[52] U.S. Cl. .................. 435/15; 435/4; 435/278; 435/885; 435/886; 435/18; 435/170; 536/1.11; 536/18.5; 536/123.12; 536/124; 536/128; 162/100

[58] Field of Search .................. 435/15, 278, 4, 435/885, 886, 18, 170; 536/123.1, 1.11, 18.5, 123.12, 124, 128; 162/100

[56] References Cited

U.S. PATENT DOCUMENTS

| | | | |
|---|---|---|---|
| 4,202,966 | 5/1980 | Misaki et al. | 536/1.11 |
| 4,342,601 | 8/1982 | Vin | 536/123.12 |
| 4,597,830 | 7/1986 | April et al. | 536/123.12 |
| 4,734,162 | 3/1988 | Ampulski | 536/123.12 |
| 5,354,424 | 10/1994 | Rha et al. | 536/123.12 |

OTHER PUBLICATIONS

Kuramitsu, et al. "Characterization of Extracellular Glucosyltransferase Activity of *Streptococcus mutans*" *Infection and Immunity*; vol. 12(4); pp. 738–749; (1975) Month not available.

Yamashita, et al. "Role of the *Streptococcus mutans* gtf Genes in Caries Induction in the Specific–Pathogen–Free Rat Model" *Infection and Immunity*; vol. 61(9); pp. 3811–3817; (1993) Month not available.

Hanada, et al. "Isolation and Characterization of the *Streptococcus mutans* gtfC Gene, Coding for Synthesis of Both Soluble and Insoluble Glucans" *Infection and Immunity*; vol. 56(8); pp. 1999–2005; (1988) Month not available.

Kametaka, et al. "Purification and Characterization of Glucosyltransferase from *Streptococcus mutans* OMZ176 with Chromatofocusing" *Microbios*; vol. 51: pp. 29–35; (1987) Month not available.

Aoki, et al. "Cloning of a *Streptococcus mutans* Glucosyltransferase Gene Coding for Insoluble Glucan Synthesis" *Infection and Immunity*; vol. 53(3); pp. 587–595; (1986) Month not available.

Shimamura, et al. "Identification of Amino Acid Residues in *Streptococcus mutans* Glycosyltransferases Influencing the Structure of the Glucan Product" *Journal Bacteriology*; vol. 176 (16); pp. 4845–4850; (1994) Month not available.

Wenham, et al. "Regulation of Glucosyl–and Fructosyltransferase Synthesis by Continuous Cultures of *Streptococcus mutans*" *J. General Microbiology*; vol. 114; pp. 117–124; (1979) Month not available.

Fu, et al. "Maltodextrin Acceptor Reactions of *Streptococcus mutans* 6715 Glucosyltransferases" *Carbohydrate Research*; vol. 217; pp. 201–211; (1991) Month not available.

Bhattacharjee, et al. "Formation of $\propto$–(1→6), $\propto$–(1→3), and $\propto$(1→2) Glycosidic Linkages by Dextransucrase from *Streptococcus sanguis* in Acceptor–Dependent Reactions" *Carbohydrate Research*; vol. 242; pp. 191–201; (1993) Month not available.

Russell, et al. "Expression of a Gene for Glucan–binding Protein from *Streptococcus mutans* in *Escherichia coli*" *J. General Microbiology*; vol. 131; pp. 295–299; (1985) Month not available.

Russell, et al. "Characterization of Glucosyltransferase Expressed from a *Streptococcus sobrinus* Gene Cloned in *Escherichia coli*" *J. General Microbiology*; vol. 133; pp. 935–944; (1987) Month not available.

Shiroza, et al. "Sequence Analysis of the gtfB Gene from *Streptococcus mutans*" *J. Bacteriology*; vol. 169(9); pp. 4263–4270; (1987) Month not available.

Müller–Röber, et al. "Inhibition of the ADP–glucose pyrophosphorylase in transgenic potatoes leads to sugar–storing tubers and influences tuber formation and expression of tuber storage protein genes" *The EMBO J.*; vol. 11(4); pp. 1229–1238; (1992) Month not available.

Creech, et al. "Carbohydrate Synthesis in Maize" *Advances in Agronomy*; vol. 20; pp. 275–322; (1968) Month not available.

Utsumi, et al. "Expression and Accumulation of Normal and Modified Soybean Glycinins in Potato Tubers" *Plant Science*; vol. 102; pp. 181–188; (1994) Month not available.

Visser, et al. "Transformation of Homozygous Diploid Potato with an *Agrobacterium tumefacies* Binary Vector System by Adventitious Shoot Regeneration on Leaf and Stem Segments" *Plant Molecular Biology*; vol. 12; pp. 329–337; (1989) Month not available.

Ebskamp, et al. "Accumulation of Fructose Polymers in Transgenic Tobacco" *Bio/Technology*; vol. 12; pp. 272–275; (1994) Month not available.

Armstrong, et al. "Regeneration of Plants from Somatic Cell Cultures: Applications for in vitro Genetic Manipulation" *The Maize Handbook*; pp. 663–671; (1994) Month not available.

Heiser, et al. "Starch Formulations" *Starch and Starch Products in Paper Coating*; pp. 147–162; (1990) Month not available.

Primary Examiner—Louise Leary

[57] ABSTRACT

The present invention provides methods of making paper utilizing glucans, produced by the glucosyltransferase C enzyme of the species *Streptococcus mutans*, instead of modified starches. The present glucans are functionally similar to the hydroxethyl modified starch and are particularly useful in the coating step of paper manufacture. The present glucans also exhibit thermoplastic properties and impart gloss to the paper during the coating step.

20 Claims, No Drawings

SUBSTITUTES FOR MODIFIED STARCH AND LATEXES IN PAPER MANUFACTURE

FIELD OF THE INVENTION

The present invention involves the field of paper manufacture. Specifically, the present invention provides sources alternative to modified starch in paper manufacture.

BACKGROUND OF THE INVENTION

There are three major phases in paper manufacture where starch is used as an ingredient. The first is the "wet end" where cellulose fibers are mixed with starch in a slurry, and the slurry is forced through a narrow opening onto a wire belt. Water is rapidly removed as the forming sheet travels the length of the belt. After a distance of typically five to fifteen meters on the belt, the sheet has had enough water removed from it so that it can support its own weight. The sheet travels through a number of foils and rolls wherein more water is removed. It is dried to about 11% moisture.

The second phase in paper manufacturing involving starch is the "sizing step". Here, the paper goes through a sizing press where a starch slurry is applied to the sheet. The sheet again goes through a series of foils and rolls. It is dried on rollers and can be taken off the press as a finished product.

The third step involves coating the paper with a mixture of starch and a thermoplastic molecule. On certain lines, this occurs after the sizing step. The nascent roll can also be removed and reinstalled onto a different press for coating. A typical coating device has two blades that run the width of the paper. The blades apply the coating material onto two rolling drums. The paper passes between the drums and the coating material, comprising starch and the thermoplastic moiety, comes off the drums onto the paper. After the paper leaves the drums, it goes through a number of dryers. When the paper is dry, it goes onto a "soft calendar" comprising two drums, one made of a hard density fabric and the other a heated steel drum. The paper passes between the two drums and the heated steel drum is sufficiently hot to melt thermoplastic components of the coating mix providing a hard gloss finish on the paper.

The cellulosic wood pulp fibers, typically used in the above process, are anionic in nature. The addition of a cationic starch to the "wet end" slurry acts as an adhesive by cross linking the pulp fibers through salt linkages. Thus a cross linked polymeric network is made, comprising the starch and cellulose fibers. Typically, the cationic starches used in the "wet end" are tertiary or quaternary amines. These amino groups are added to the starch by wet millers.

Surface sizing starches are used to impart both strength and smooth finish to the sheet after it leaves the "wet end". Such starches also prepare the sheet to receive the various coatings. In cheaper grades of paper and in fiberboard manufacture, sizing starches are used simply as unmodified corn starch. For high grades of paper, chemically-modified starches are used. This is important for the application of a smooth, uniform high quality surface to the paper.

There is a tendency for starches to retrograde i.e. re-form high ordered structures (both helices and crystallites) in an otherwise gelatinous starch slurry. Deposition of retrograded starch onto high quality paper causes regional inconsistencies on the paper and is unacceptable. Furthermore, retrograded starch in the sizing press may necessitate shutting the line down to clear the apparatus.

The starch most often used for sizing applications is a starch having a covalently attached neutral adduct, for instance hydroxyethyl starch. This is prepared by the reaction of ethylene oxide with starch after it is isolated at the wet milling plant. The function of the hydroxyethyl (or similar) adduct is independent of its chemical nature; rather, it serves to provide steric hindrance, inhibiting the formation of high ordered structures. This steric hindrance is critical to decrease retrogradation. The periodic protuberance afforded by the adduct disrupts the formation of higher ordered structures that leads to retrogradation.

Speed is of paramount importance in paper manufacturing. Limiting in press speed is starch consistency. Presses often run below their full capacity speeds. Depending on the application, starch slurries are between 3–15% (usually 5–6%) solids. An increase in solids would necessarily result in a decrease in the amount of water that would have to be removed from a paper sheet being manufactured. This would allow the press to work at higher speeds.

Hydroxethylated starch also forms higher ordered structures as the temperature decreases or the concentration increases. The formation of the higher ordered structures on the surface of the paper is required. After application to the sheet the starch reforms some of these higher ordered structures and creates a uniform surface that imparts structural strength and facilitates the acceptance of inks and dyes. However, the higher ordered structures should not form in the slurry nor on the application device because this necessitates shutting down the production line to clear off retrograded starch.

The function of the hydroxyethyl group is to lower the temperature and/or raise the concentration of starch at which retrogradation occurs. As the processing lines have already been optimized for a particular temperature of the starch slurry, a decrease in the tendency to retrograde would allow for a higher carbohydrate content in the slurry.

The mixture applied to the paper sheet in the coating process contains hydroxethylated starch and thermoplastic molecules. The most prevalent thermoplastic molecules used are latexes, such as styrene butadiene. The function of the hydroxethyl starch is as indicated above. The function of the thermoplastic molecule is to form a high gloss finish on the paper. This causes an increased ability to take inks and dyes and improves the resolution, in general, on the printed sheet.

Based on the foregoing, there exists a need, in paper manufacturing, for modified starch substitutes which are functionally similar to modified starch. There is a further need to provide substitutes for modified starch which are less prone to retrogradation. There is a further need to provide methods of manufacturing paper which are faster than current methods and allow presses to run closer to their full capacity speed. There is a further need to provide methods of manufacturing paper that are environmentally-friendly and do not involve input materials that require chemical processing.

It is therefore an object of the present invention to provide substitutes for modified starch which are less prone to retrogradation when used in paper manufacture.

It is a further object of the present invention to provide methods of manufacturing paper which are faster and more efficient than existing methods.

It is a further object of the present invention to provide substitutes for starch in paper manufacturing that do not require costly chemical modification as does starch.

It is a further object of the present invention to provide methods for manufacturing paper that are more environmentally-friendly than existing methods.

It is a further object of the present invention to provide substitutes for thermoplastic molecules currently used in the coating step during paper manufacture.

SUMMARY OF THE INVENTION

The present invention provides glucans which can be used as substitutes for modified starch and latexes in paper manufacture. The present glucans are produced by the glucosyltransferase C ("GTF C") enzyme of the species *Streptococcus mutans*, and are functionally similar to the modified starch currently used in paper manufacture. The present glucans also exhibit similar physical properties to thermoplastic molecules currently used in the coating step during paper manufacture.

The present invention also provides methods of making paper utilizing the present glucans, input materials that are produced biologically. Thus, the present methods are more cost-effective and environmentally-friendly than current methods, which require input materials that produce chemical effluents.

DETAILED DESCRIPTION OF THE INVENTION

As used herein "glucan" means a glucose polymer having linkages that are $\alpha(1\to3)$, $\alpha(1\to6)$ and branching $\alpha(1\to3,6)$.

As used herein "amyloplast" means starch accumulating organelle in plant storage tissue.

As used herein, "vacuole" means the cellular compartment bounded by the tonoplast membrane. *Streptococcus mutans* is a species that is endogenous to the oral cavity and colonizes tooth enamel. See e.g. Kuramitsu, et al., "Characterization of Extracellular Glucosyl Transferase Activity of *Streptococcus-mutans*," *Infect. Immun.*; Vol. 12(4); pp. 738–749; (1975); and Yamashita, et al., "Role of the *Streptococcus-mutans-gtf* Genes in Caries Induction in the Specific-Pathogen-Free Rat Model," *Infect. Immun.*; Vol. 61(9); pp. 3811–3817; (1993); both incorporated herein their entirety by reference. *Streptococcus mutans* species secrete the glucosyltransferase C ("GTF C") enzyme which utilizes dietary sucrose to make a variety of extracellular glucans. See e.g. Hanada, et al., "Isolation and Characterization of the *Streptococcus mutans* gtfc Gene, Coding for Synthesis of Both Soluble and Insoluble Glucans," *Infect. Immun.*; Vol. 56(8); pp. 1999–2005; (1988); and Kametaka, et al., "Purification and Characterization of Glucosyltransferase from *Streptococcus-mutans* OMZ176 with Chromatofocusing," *Microbios*; Vol. 51(206); pp. 29–36; (1978); both incorporated herein in its entirety by references.

Both soluble and insoluble glucans are synthesized, and the proteins responsible have been isolated and characterized. See e.g. Aoki, et al., "Cloning of a *Streptococcus-mutans* Glucosyltransferase Gene Coding for Insoluble Glucan Synthesis" *Infect. Immun.*, Vol. 53 (3); pp. 587–594; (1986); Shimamura, et al., "Identification of Amino Acid Residues in *Streptococcus mutans* Glucosyltransferases Influencing the Structure of the Glucan Produced," *J. Bacteriol.*; Vol. 176(16); pp. 4845–50; (1994); and Kametaka, et al., "Purification and Characterization of Glucosyltransferase from *Streptococcus-mutans* OMZ176 with Chromatofocusing," *Microbios*; Vol. 51 (206); pp. 29–36; (1987); all incorporated herein their entirety by reference.

The proteins involved are large (~155 kDa) and catalyze the group transfer of the glucosyl portion of sucrose to an acceptor glucan via $\alpha(1\to3)$ and $\alpha(1\to6)$ linkages. See e.g. Wenham, et al., "Regulation of Glucosyl Transferase and Fructosyl Transferase Synthesis by Continuous Cultures of *Streptococcus-mutans*," *J. Gen Microbiol.*; Vol. 114 (Part 1); pp. 117–124; (1979); and Fu, et al., "Maltodextrin Acceptor Reactions of *Streptococcus-mutans* 6715 glucosyltransferases," *Carbohydr. Res.*; Vol. 217; pp. 210–211; (1991); and Bhattacharjee, et al., "Formation of Alpha—$(1\to6)$, Alpha—$(1\to3)$, and Alpha $(1\to2)$ Glycosidic Linkages by Dextransucrase from *Streptococcus Sanguis* in Acceptor-Dependent Reactions," *Carbohydr. Res.*, Vol. 242; pp. 191–201; (1993); all incorporated herein their entirety by reference.

The genes involved in glucan synthesis have been isolated and sequenced. See Shimamura, et al., cited hereinabove and Russel, et al., "Expression of a Gene for Glucan-binding Protein from *Streptococcus-mutans* in *Escherichia-coli*," *J. Gen. Microbiol.*; Vol. 131(2); pp. 295–300; (1985); Russell, et al., "Characterization of Glucosyltransferase Expressed from a *Streptococcus-sobrinus* Gene Cloned in *Escherichia-coli*," *J. Gen. Microbiol.*; Vol. 133(4); pp. 935–944; (1987); and Shiroza, et al., "Sequence Analysis of the gtfc Gene from *Streptococcus mutans*," *J. Bacteriol.*; Vol. 169(9); pp. 4263–4270; (1987); all incorporated herein in their entirety by reference.

The structure of the glucans produced by the GTF C enzyme is quite heterogeneous with respect to the proportions of $\alpha(1\to3)$, $\alpha(1\to6)$ and $\alpha(1\to3,6)$ branches present in any given glucan. Transformation of genes which encode naturally occurring GTF C into plants, such as maize, provides amyloplasts and vacuoles with novel compositions.

GTF C enzyme activity incorporated into the amyloplast and/or vacuole leads to the accumulation of starch and glucan in the same amyloplast and/or vacuole. Retrogradation occurs as portions of starch molecules interact and subsequently form inter- or intra-chain helices. In a mixture of starch and glucans, the frequency of starch-starch interactions that lead to helix formation is diminished. A paste made from the mixed polymers is less prone to retrogradation as a result. This is especially true in the starch accumulation mutants envisioned as transformation targets where the relative proportion of starch is reduced.

Glucans produced in maize amyloplasts and/or vacuoles by the transgenic GTF C enzyme can function in paper processing without chemical modification, as required of starch. The polymer solution consequently has altered rheological properties and is less prone to retrogradation compared to starch. The glucans are branched and irregular and able to supplant modified starches with comparable or superior efficacy. They do not require any costly chemical modification as does starch. For coating applications, the present glucans exhibit thermoplastic properties in addition to the above advantages.

The wild type of GTF C is useful in producing glucans according to the present invention. The GTF C enzyme is well known. See e.g. Shimamura et al., and Hanada, et al., cited hereinabove. The glucans produced are particularly useful as substitutes for modified starches in the coating step of paper manufacture. The present glucans are also useful as substitutes for thermoplastic molecules such as latex (e.g. styrene butadiene). The subject glucans impact a high gloss finish on the paper and increase the ability of the paper to take on dyes and inks and improves the resolution in general on the printed sheet.

The glucans of the present invention are preferably produced in transgenic maize, potato, cassava, sweet potato, rye, barley, wheat, sorghum, oats, millet, triticale, sugarcane and rice. More preferably, the present glucans are produced in maize, potato, sugarcane, cassava, and sweet potato. Even more preferably, the present glucans are produced in maize and potato. Most preferably, the present glucans are produced in maize.

In a highly preferred embodiment of the present invention, maize lines deficient in starch biosynthesis are transformed with GTF C genes. Such lines may be naturally occurring maize mutants (i.e. $sh_2$, $bt_2$, $bt_1$) or transgenic maize engineered so as to accumulate low amounts of starch in the endosperm when compared to wild type maize. See e.g. Müller-Röber, et al., "Inhibition of the ADP-glucose Pyrophosphorylase in Transgenic Potatoes Leads to Sugar-Storing Tubers and Influences Tuber Formation and Expression of Tuber Storage Protein Genes," *The EMBO Journal*; Vol. 11(4); pp. 1229–1238; (1992); and Creech, "Carbohydrate Synthesis in Maize," *Advances in Agronomy*; Vol. 20; pp. 275–322; (1968); both incorporated herein in their entirety by reference.

The production of the present glucans is performed according to methods of transformation that are well known in the art, and thus constitute no part of this invention. The compounds of the present invention are synthesized by insertion of an expression cassette containing a synthetic gene which, when transcribed and translated, yields a GTF enzyme that produces the desired glucan. Such empty expression cassettes, providing appropriate regulatory sequences for plant expression of the desired sequence, are also well-known, and the nucleotide sequence for the synthetic gene, either RNA or DNA, can readily be derived from the amino acid sequence for the protein using standard texts and the references provided. The above-mentioned synthetic genes preferably employ plant-preferred codons to enhance expression of the desired protein.

The following description further exemplifies the compositions of this invention and the methods of making and using them. However, it will be understood that other methods, known by those of ordinary skill in the art to be equivalent, can also be employed.

The genes which code for the present enzyme can be inserted into an appropriate expression cassette and introduced into cells of a plant species. Thus, an especially preferred embodiment of this method involves inserting into the genome of the plant a DNA sequence coding for a mutant or wild type in proper reading frame, together with transcription promoter and initiator sequences active in the plant. Transcription and translation of the DNA sequence under control of the regulatory sequences causes expression of the protein sequence at levels which provide an elevated amount of the protein in the tissues of the plant.

Synthetic DNA sequences can then be prepared which code for the appropriate sequence of amino acids of GTF C protein, and this synthetic DNA sequence can be inserted into an appropriate plant expression cassette.

Plant expression cassettes and vectors applicable in the present invention are well known in the art. By the term "expression cassette" is meant a complete set of control sequences including promoter, initiation, and termination sequences which function in a plant cell when they flank a structural gene in the proper reading frame. Expression cassettes frequently and preferably contain an assortment of restriction sites suitable for cleavage and insertion of any desired structural gene. It is important that the cloned gene have a start codon in the correct reading frame for the structural sequence.

By the term "vector" herein is meant a DNA sequence which is able to replicate and express a foreign gene in a host cell. Typically, the vector has one or more restriction endonuclease recognition sites which may be cut in a predictable fashion by use of the appropriate enzyme such vectors are preferably constructed to include additional structural gene sequences imparting antibiotic or herbicide resistance, which then serve as markers to identify and separate transformed cells. Preferred markers/selection agents include kanamycin, chlorosulfuron, phosphonothricin, hygromycin and methotrexate. A cell in which the foreign genetic material in a vector is functionally expressed has been "transformed" by the vector and is referred to as a "transformant".

A particularly preferred vector is a plasmid, by which is meant a circular double-stranded DNA molecule which is not a part of the chromosomes of the cell.

As mentioned above, both genomic DNA and cDNA encoding the gene of interest may be used in this invention. The gene of interest may also be constructed partially from a cDNA clone and partially from a genomic clone. When the gene of interest has been isolated, genetic constructs are made which contain the necessary regulatory sequences to provide for efficient expression of the gene in the host cell. According to this invention, the genetic construct will contain (a) a genetic sequence coding for the protein or trait of interest and (b) one or more regulatory sequences operably linked on either side of the structural gene of interest. Typically, the regulatory sequences will be selected from the group comprising of promoters and terminators. The regulatory sequences may be from autologous or heterologous sources.

The expression cassette comprising the structural gene for a mutant of this invention operably linked to the desired control sequences can be ligated into a suitable cloning vector. In general, plasmid or viral (bacteriophage) vectors containing replication and control sequences derived from species compatible with the host cell are used. The cloning vector will typically carry a replication origin, as well as specific genes that are capable of providing phenotypic selection markers in transformed host cells. Typically, genes conferring resistance to antibiotics or selected herbicides are used. After the genetic material is introduced into the target cells, successfully transformed cells and/or colonies of cells can be isolated by selection on the basis of these markers.

Typically, an intermediate host cell will be used in the practice of this invention to increase the copy number of the cloning vector. With an increased copy number, the vector containing the gene of interest can be isolated in significant quantities for introduction into the desired plant cells. Host cells that can be used in the practice of this invention include prokaryotes, including bacterial hosts such as *E. coli*, *S. typhimurium*, and *Serratia marcescens*. Eukaryotic hosts such as yeast or filamentous fungi may also be used in this invention. Since these hosts are also microorganisms, it will be essential to ensure that plant promoters which do not cause expression of the protein in bacteria are used in the vector.

The isolated cloning vector will then be introduced into the plant cell using any convenient technique, including electroporation (in protoplasts), retroviruses, bombardment, and microinjection into cells from monocotyledonous or dicotyledonous plants in cell or tissue culture to provide transformed plant cells containing as foreign DNA at least one copy of the DNA sequence of the plant expression cassette. Using known techniques, protoplasts can be regenerated and cell or tissue culture can be regenerated to form whole fertile plants which carry and express the gene for a protein according to this invention. Accordingly, a highly preferred embodiment of the present invention is a transformed maize plant, the cells of which contain as foreign DNA at least one copy of the DNA sequence of an expression cassette of the GTF C protein.

It will also be appreciated by those of ordinary skill that the plant vectors provided herein can be incorporated into *Agrobacterium tumefaciens*, which can then be used to transfer the vector into susceptible plant cells, primarily from dicotyledonous species. Thus, this invention provides a method for introducing GTF C in *Agrobacterium tumefaciens*-susceptible dicotyledonous plants in which the expression cassette is introduced into the cells by infecting the cells with *Agrobacterium tumefaciens*, a plasmid of which has been modified to include a plant expression cassette of this invention.

For example, the potato plant can be transformed via *Agrobacterium tumefaciens* to produce the present glucans. The transformation cassette comprises a patatin promoter, followed by the GTF C coding sequence and the neomycin phosphotransferase polyadenylation site/terminator. See e.g. Utsumi, et al., "Expression and Accumulation for Normal and Modified Soybean Glycinins in Potato Tubers," *Plant Science*; Vol. 102(2); pp. 181–188; (1994); (Limerick); incorporated herein in its entirety by reference. The transgenic cassette is placed into a transformation vector. For example, BIN19, or derivatives thereof, are useful when transforming via *Agrobacterium tumefaciens*. See e.g. Visser, et al., "Transformation of Homozygous Diploid Potato with an *Agrobacterium-tumefaciens* Binary Vector System by Adventitious Shoot Regeneration on Leaf and Stem Segments," *Plant Mol. Biol.*; Vol. 12(3); pp. 329–338; (1989); incorporated herein in its entirety by reference.

For maize transformation vectors, the promoters include any promoter whose expression is specific and limited to endosperm cells. Included are those encoding either 22 kDa zein, opaque2, gamma zein and waxy. These lead into the GTF C gene and are followed by the endogenous terminator or the heterogeneous PINII terminator.

The GTF C protein is directed to the maize endosperm amyloplast using a suitable transit sequence. Transit sequences useful in directing the enzyme into the amyloplast for accumulation within the amyloplast include but are not limited to ribulose biphosphate carboxylase small subunit, waxy, brittle-1, and chlorophyll AB binding protein. The transit sequences are juxtaposed between the promoter and the GTF C coding sequence and fused in translational reading frame with the GTF C moiety.

Transit sequences useful in directing the enzyme into the vacuole for accumulation within the vacuole are well known in the art. For vacuolar targeting, see e.g. Ebskamp, et al., "Accumulation of Fructose Polymers in Transgenic Tobacco," *Bio/technology*; Vol. 12; pp. 272–275; (1994); incorporated herein in its entirety by reference.

For maize transformation and regeneration see e.g. Armstrong, C., (1994), "Regeneration of Plants from Somatic Cell Cultures: Applications for in vitro Genetic Manipulation," *The Maize Handbook*, Freeling, et al. eds, pp. 663–671; incorporated herein in its entirety by reference.

Once a given plant is transformed, the glucans synthesized can be isolated, by standard methods, known to one skilled in the art. The glucans thus obtained in the transgenic plant can be substituted for modified starches and utilized in the sizing and/or coating steps. For formulations useful in the coating step, see e.g. Heiser, et al., "Starch Formations," *Starch and Starch Products in Paper Coating*; Kearney, et al., eds., pp. 147–162; (1990); Tappi Press; incorporated herein in its entirety by reference.

The present glucans are utilized in an amount of from about 4 to about 15 weight percent, more preferably from about 5 to about 12 weight percent, also preferably from about 6 to about 8 weight percent. Weight percent is defined as grams of molecule per 100 ml coating solution.

The present glucans are used to replace the starch and/or latex molecules completely, or a starch-glucan or a latex-glucan mixture is used in the slurry. In the coating application, the glucan:starch ratio preferably ranges from about 10:90 to about 100:0; more preferably from about 40:60 to about 100:0; more preferably still from about 60:40 to about 100:0; most preferably about 100:0. The glucan:latex ratio preferably ranges from about 10:90 to about 100:0; more preferably from about 40:60 to about 100:0; more preferably still from about 60:40 to about 100:0; most preferably about 100:0.

All publications cited in this application are indicative of the level of skill of those skilled in the art to which this invention pertains. All publications are herein incorporated by reference to the same extent as if each individual publication or patent application was specifically and individually indicated to be incorporated by reference.

Variations on the above embodiments are within the ability of one of ordinary skill in the art, and such variations do not depart from the scope of the present invention as described in the following claims.

What is claimed is:

1. A method of manufacturing paper comprising adding a glucan isolated from a host transformed with a gene encoding a glucosyltransferase C (GTFC) obtained from *Streptococcus mutans*, to one or more of the steps of (A) wet ending, (B) sizing, and (C) coating in paper manufacturing wherein modified starch is used.

2. The method of claim 1 wherein the glucan is added to the coating step.

3. The method of claim 2 wherein the amount of glucan utilized is from about 4 to about 15 weight percent of the coating composition.

4. The method of the claim 3 wherein the glucan is produced in a plant selected from the group consisting of maize, potato, cassava, sweet potato, rye, barley, sugarcane, wheat, sorghum, oats, millet, triticale and rice.

5. The method of claim 4 wherein the glucan is produced by transformation with *Agrobacterium tumefaciens*, microparticle injection, electroporation, bombardment or retroviruses.

6. The method of claim 3 wherein the amount of glucan utilized is from about 5 to about 12 weight percent of the coating composition.

7. The method of claim 5 wherein the transformation is performed using a transit sequence selected from the group consisting of ribulose biphosphate carboxylase small subunit, waxy, brittle-1 and chlorophyll AB binding protein to produce a transgenic plant.

8. The method of claim 7 wherein the transgenic plant has been genetically engineered to down regulate or abolish starch biosynthesis.

9. The method of claim 8 wherein the glucan is produced in potato or maize.

10. The method of claim 9 wherein the GTF C is produced by using a promoter selected from the group consisting of 22 kDa zein, opaque 2, gamma zein and waxy.

11. The method of claim 10 wherein the glucan is produced in the amyloplast of maize.

12. A method of imparting gloss on paper during the manufacturing process comprising adding a glucan isolated from a host transformed with a gene encoding a glucosyltransferase C enzyme obtained from *Streptococcus mutans* to a coating step instead of latex molecules.

13. The method of claim 12 wherein the amount of glucan utilized is from about 4 to about 15 weight percent of the coating composition.

14. The method of claim 13 wherein the glucan is produced in a plant selected from the group consisting of maize, potato, cassava, sweet potato, sugarcane, rye, barley, wheat, sorghum, oats, millet, triticale, and rice.

15. The method of claim 14 wherein the glucan is produced by a transformation with *Agrobacterium tumefaciens*, electroporation, microparticle injection, bombardment or retroviruses.

16. The method of claim 15 wherein the amount of glucan utilized is from about 5 to about 12 weight percent of the coating composition.

17. The method of claim 16 wherein the transformation is performed using a transit sequence selected from the group consisting of ribulose biphosphate carboxylase small subunit, waxy, brittle-1, and chlorophyll AB binding protein.

18. The method of claim 17 wherein the glucan is produced in potato or maize.

19. The method of claim 18 wherein the glucan is produced by using a promoter selected from the group consisting of 22 kDa zein, opaque 2, gamma zein and waxy.

20. An isolated glucan obtained from the amyloplast or vacuole of a transgenic plant transformed with a gene encoding a glucosyltransferase C enzyme from *Streptococcus mutans*.

* * * * *